(12) United States Patent
Looten et al.

(10) Patent No.: US 9,346,722 B2
(45) Date of Patent: May 24, 2016

(54) METHOD FOR REFINING SQUALENE PRODUCED BY MICROALGAE

(71) Applicant: ROQUETTE FRERES, Lestrem (FR)

(72) Inventors: Philippe Looten, Lomme (FR); Samuel Patinier, Lille (FR); Michel Perrut, Villers les Nancy (FR); Vincent Perrut, Venterol (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 14/394,813

(22) PCT Filed: Apr. 15, 2013

(86) PCT No.: PCT/FR2013/050812
§ 371 (c)(1),
(2) Date: Oct. 16, 2014

(87) PCT Pub. No.: WO2013/156720
PCT Pub. Date: Oct. 24, 2013

(65) Prior Publication Data
US 2015/0140030 A1    May 21, 2015

(30) Foreign Application Priority Data

Apr. 16, 2012  (FR) .................. 12 53496
Apr. 19, 2012  (FR) .................. 12 53614

(51) Int. Cl.
| | |
|---|---|
| C12P 7/64 | (2006.01) |
| C07C 7/08 | (2006.01) |
| A23L 1/30 | (2006.01) |
| A23L 1/337 | (2006.01) |
| A61Q 19/00 | (2006.01) |
| B01D 11/04 | (2006.01) |
| C11B 1/10 | (2006.01) |
| C12P 5/00 | (2006.01) |
| A61K 8/31 | (2006.01) |
| A61K 8/97 | (2006.01) |
| A61K 31/01 | (2006.01) |
| A61K 36/02 | (2006.01) |
| B01D 3/40 | (2006.01) |
| C07C 5/03 | (2006.01) |

(52) U.S. Cl.
CPC ............... *C07C 7/08* (2013.01); *A23L 1/3002* (2013.01); *A23L 1/337* (2013.01); *A61K 8/31* (2013.01); *A61K 8/975* (2013.01); *A61K 31/01* (2013.01); *A61K 36/02* (2013.01); *A61Q 19/00* (2013.01); *B01D 3/40* (2013.01); *B01D 11/0403* (2013.01); *B01D 11/0426* (2013.01); *C07C 5/03* (2013.01); *C11B 1/104* (2013.01); *C12P 5/007* (2013.01); *A61K 2800/10* (2013.01); *A61K 2800/85* (2013.01); *A61K 2800/86* (2013.01); *Y02E 50/343* (2013.01); *Y02P 20/544* (2015.11)

(58) Field of Classification Search
CPC ........................................................ C07C 7/08
See application file for complete search history.

(56) References Cited

U.S. PATENT DOCUMENTS

| | | | |
|---|---|---|---|
| 7,575,767 B2 * | 8/2009 | May ................. | C07D 311/72 424/776 |
| 2004/0015033 A1 | 1/2004 | Steiner et al. | |
| 2011/0243969 A1 | 10/2011 | Broeker | |

FOREIGN PATENT DOCUMENTS

| | | |
|---|---|---|
| CN | 102 100 260 | 6/2011 |
| EP | 0 541 999 | 5/1993 |
| EP | 1 818 388 | 8/2007 |
| WO | WO 2005/075614 | 8/2005 |
| WO | WO 2008/142175 | 11/2008 |

OTHER PUBLICATIONS

Lu et al (Journal of Chromatography A, 994, pp. 37-43, 2003).*
Chen, G. et al. "Optimization of nitrogen source for enhanced production of squalene from thraustochytrid *Aurantiochyrium* sp." *New Biotechnology*, Sep. 2010, pp. 382-389, vol. 27, No. 4.
Written Opinion in International Application No. PCT/FR2013/050812, Oct. 14, 2013, pp. 1-8.

* cited by examiner

*Primary Examiner* — Albert Navarro
(74) *Attorney, Agent, or Firm* — Saliwanchik, Lloyd & Eisenschenk

(57) ABSTRACT

The invention relates to a method for preparing a composition that is very rich in squalene produced by fermentation of micro-organisms. The method is characterized in that it comprises a purification step selected from the group including: supercritical $CO_2$ extraction in a multi-stage counter-current fractionation column with extract reflux, and short-path molecular distillation.

13 Claims, No Drawings

METHOD FOR REFINING SQUALENE PRODUCED BY MICROALGAE

CROSS-REFERENCE TO RELATED APPLICATION

This application is the U.S. national stage application of International Patent Application No. PCT/FR2013/050812, filed Apr. 15, 2013.

The present invention relates to a method for refining squalene produced by fermentation, starting from microorganisms, more particularly microalgae, even more particularly those from the family Thraustochytriales sp.

In the sense of the invention, "microalgae of the family Thraustochytriales sp." means microalgae belonging to the species *Schizochytrium* sp., *Aurantiochytrium* sp. and *Thraustochytrium* sp.

Squalene is a lipid present in all higher organisms, and is the common precursor of steroid hormones, both animal and vegetable, and of some vitamins, such as the D vitamins.

It is present in many cell membranes, thus providing them with fluidity.

This unsaturated linear hydrocarbon is an isoprenoid with thirty carbon atoms and fifty hydrogen atoms, of formula: 2,6,10,15,19,23-hexamethyl-2,6,10,14,18,22-tetracosahexene, $C_{30}H_{50}$, i.e. it consists of 6 isoprene units, all in trans conformation.

Like all the terpenes, it is formed from isopentyl pyrophosphate, which couples with dimethylallyl pyrophosphate to supply successively the geranyl pyrophosphates, then the farnesyl pyrophosphates, two molecules of which condense after reduction by NADPH to form squalene under the action of squalene synthase.

In plants and numerous microorganisms, this pathway coexists with other metabolic pathways leading to phytoene, the precursor of chlorophyll, of carotenoid pigments and of the terpenes in lattices.

Squalene, and its derivative epoxidized on the terminal double bond, possess the property of being transformed, owing to specialized enzymes (the cyclases), remarkably regio- and stereoselectively, into polycyclic triterpenes of considerable structural variety: hopene and diplopterol in the eukaryotes and tetrahymanol in the protozoa (pentacyclic triperpenes); lanosterol in the yeasts, fungi and mammals and cycloartenol in plants (tetracyclic triperpenes).

The Applications of Squalene

Squalene has long been used, notably in Japan, as a food supplement.

Moreover, it was a Japanese chemist, Mitsumaru Tsujimoto, who discovered it in 1906 and determined its structure in 1916.

It is considered to be an effective antioxidant, with many beneficial properties in natural medicines.

Its conventional uses include cosmetics, although there it is commoner to use its hydrogenated derivative, squalane, which does not oxidize, and therefore does not become rancid.

When it is of high purity, combined with adjuvants that stimulate the immune system, squalene has been, and still is, used in certain vaccines: in the form of "oil-in-water" emulsion, it acts as a surfactant, thus increasing the response of the vaccine.

It is used in experimental vaccines targeting emerging viruses, such as H5N1 and H1N1, but especially in combination with the antigens of seasonal influenza, in the composition of the 22 million doses administered since 1997 (MF59 at a rate of 10 mg per dose of FLUAD®), without serious postvaccinal reactions.

Addition of adjuvants, squalene or aluminum salts (used since 1926) is necessary at present for certain vaccines which, being inactivated or subunit vaccines, do not contain the signals enabling the immune system to employ the appropriate defense mechanisms.

Squalene avoids the need for repeated injections to ensure good protection.

These uses of squalene reinforce the determination of a person skilled in the art to have secure methods for producing squalene of high purity.

Moreover, this quality may open up other routes of application in the medical field.

Chemical coupling of squalene with nucleoside analogs might thus constitute, in the future, a considerable advance in the treatment of certain cancers or in viral diseases of the HIV type.

The Various Sources of Squalene

Squalene is extracted conventionally from deep-sea shark livers.

However, the liver accumulates numerous toxic compounds, such as heavy metals (including mercury) and other fat-soluble toxins.

Toxicological studies have shown that at the concentrations used in cosmetics, squalene and its hydrogenated form squalane are not toxic and are not irritant or sensitizing for human skin.

However, the level of purity of squalene is essential when used in the medical field, notably as an adjuvant for vaccines.

It is therefore absolutely essential to have squalene of high quality, free from impurities (traces of metals, notably mercury, and other toxins).

Several routes for production of squalene, other than its extraction from shark livers, are proposed in the literature.

As a first alternative, it may be isolated from olive oil, palm oil, and other cereal oils or oils derived from amaranth, seeds, rice bran, and wheat germ.

However, the major drawback here is that squalene is extracted from these in very small amounts, on the order of 0.1 to 0.7 wt %, and requires a great many arduous and expensive purification steps.

As a second alternative, first methods of production of squalene have been proposed from microorganisms, more particularly from natural yeasts or recombinant yeasts, notably of the *Saccharomyces* type.

Thus, *Saccharomyces cerevisiae* is known to be able to produce squalene, but in very small amounts: on the order of 0.041 mg/g of biomass (BHATTACHARJEE, P. et al., 2001, *World J. Microb. Biotechnol.*, 17, pp 811-816).

Optimization of these capacities for production has therefore been attempted by means of genetic recombination.

However, as presented in patent application WO 2010/023551 for the medical field (production of squalene of purity above 97% as an adjuvant for vaccines), this first alternative can only be applied industrially if recombinant yeasts that overproduce squalene (at more than 15 wt % of dry cells) are available.

Now, obtaining these recombinant cells requires the application of numerous arduous, long and complex steps of metabolic engineering, by employing tools of molecular biology, leading to stimulation of the squalene biosynthesis pathways and to inhibition of the squalene catabolism pathways.

In fact, as is moreover recalled in said patent application WO 2010/023551, multiple genes are involved in the biosynthesis of squalene: including mevalonate kinase, phosphomevalonate kinase, pyrophosphomevalonate decarboxylase, isopentenyl pyrophosphate isomerase, HMGR (3-hydroxy-3-methylglutaryl-CoA reductase), and squalene synthetase.

For the catabolism pathways, the genes coding for numerous enzymes involved in the conversion of squalene to ergosterol include squalene epoxidase (ERG1), lanosterol synthetase, C14-dimethylase, d14-reductase, C4-methyloxidase, C4-decarboxylase (ERG26), 3-ketoreductase, C24-methyltransferase, C8-isomerase, C5-desaturase, d22-desaturase and d24-reductase.

Moreover, other catabolic enzymes must also be considered: LEU2 ([beta]-isopropylmalate dehydrogenase), oxidosqualene cyclase, zymosterol-24-methyltransferase and ergosta-5,7,24(28)-trienol-22-dehydrogenase.

As a third alternative to the methods of extraction from shark livers, promising methods have been proposed for production of squalene from microalgae, notably of the family Thraustochytriales (comprising the genera *Thraustochytrium, Aurantiochytrium* and *Schizochytrium*), more particularly *Schizochytrium mangrovei* or *Schizochytrium limacinum*.

Moreover, these microalgae produce squalene in heterotrophic conditions (absence of light; supply of glucose as carbon-containing source), and may therefore be manipulated easily by a person skilled in the art of fermentation of microorganisms.

In these microalgae of the family Thraustochytriales, squalene is, however, the coproduct of other lipid compounds of interest, such as docosahexaenoic acid (DHA), a polyunsaturated fatty acid of the $\omega 3$ family.

It thus appears that squalene is described especially as one of the components of the unsaponifiable fraction of the commercial oils of DHA (besides carotenoids and sterols).

For comparison, the FB1 strain of *Schizochytrium mangrovei* produces DHA at a rate of 6.2% dry weight of cells, to 0.017% of squalene.

Accordingly, these microorganisms that produce squalene naturally do so in small amounts:
  on the order of 0.1 mg/g of biomass, for Thraustochytrid ACEM 6063 (cf. LEWIS et al., Mar. Biotechnol., 2001, pp 439-447),
  on the order of 0.162 mg/g of biomass, for *Schizochytrium mangrovei* FB1 (cf. JIANG et al., J. Agric. Food Chem., 2004, 52, pp 1196-1200).

However, through optimization of production by fermentation, specialists in this field have succeeded in producing on the order of:
  1 mg to 1.2 mg of squalene per g of biomass of Thraustochytrid ACEM 6063 (cf. QIAN Li et al., *J. Agric. Food Chem.*, 2009, 57, 4267-4272 or LEWIS et al., *Mar. Biotechnol.*, 2001, 3, 439-447).
  0.72 mg of squalene per g of biomass of *Schizochytrium* (cf. G. CHEN et al., *New Biotechnology*, 2010, 27-4, pp 382-389).
  0.53 mg of squalene per g of biomass of *Aurantiochytrium mangrovei* FB31 (cf. K. W. FAN et al., *World J. Microbiol. Biotechnol.*, 2010, 26-3, pp 1303-1309).
  1.17±0.6 mg of squalene per g of biomass of *Schizochytrium mangrovei* (cf. C-J YUE and Y. JIANG, Process Biochemistry, 2009, 44, 923-927).

The applicant has also contributed to further improvement in the production of squalene by microalgae of the family Thraustochytriales sp., offering a method for producing squalene at a level never previously reached in the literature in this field, i.e. of at least 8 g of squalene per 100 g of biomass (in its French patent applications under examination).

Thus, although the microalgae of the family Thraustochytriales sp. now allow production of squalene in appreciable amounts, it is still necessary to refine it to meet food, cosmetic and especially medical requirements.

A certain number of methods of purification of squalene are proposed in the literature, but these methods are adapted by a person skilled in the art to the conventional sources of production of squalene (animal, plant or microorganism of the yeast type).

Four main technologies are generally employed, alone or in combination:
  crystallization,
  chromatography,
  distillation or
  extraction using supercritical fluid (such as supercritical $CO_2$).

As will be explained below, the two last-mentioned technologies are those that are encountered most often.

For purification of squalene of vegetable origin, for example in patent application US 2003/130532 a method is claimed for extracting the unsaponifiable substances from a vegetable oil comprising at least one saponification step, by which said oil is transformed into an aqueous-alcoholic solution, a step of countercurrent extraction of the aqueous-alcoholic solution with an organic solvent such as chloro-1-butane, a step of crystallization of the sterols and/or triterpene alcohols coproduced and finally isolation of squalene by distillation.

Preferably, the vegetable oil treated is an avocado oil or soybean oil.

In international patent application WO 2010/004193, also starting from plants, to avoid the use of organic solvents, for example an overall method is described for extracting sterols, vitamin E, squalene and other hydrocarbons from distillates from deodorization of vegetable oils.

After esterification of the free fatty acids, and then transesterification of the combined fatty acids (glycerides and sterides) with the same "short" alcohol, three successive distillations allow successive recovery of the hydrocarbons, then the alkyl esters, and finally the heaviest alkyl esters with the squalene.

The third distillate thus serves for production of squalene, which will be isolated from a first fraction, with a second fraction of residual hydrocarbons.

The residue from the third distillation will serve for production of sterols and vitamin E.

The method therefore makes it possible to extract each of the four unsaponifiable substances without any solvent of petroleum origin and to claim the label of products obtained by natural physical and chemical methods.

However, as noted above, these methods of extraction of vegetable squalene are still difficult to extrapolate to an industrial scale, either owing to the use of toxic solvents, or owing to an unattractive price.

The methods for purification of squalene produced by microorganisms of the *S. cerevisiae* type conventionally they employ methods of solvent extraction.

A first extraction step is generally carried out with methanol/chloroform (2:1) on the lipids recovered after cell lysis, followed by a chromatography step.

For its part, extraction with supercritical $CO_2$ is often preferred in order to minimize the use of organic solvents, as described for example in the article of BHATTACHARJEE and SINGHAL, in *World Journal of Microbiology and Biotechnology*, 2003, 19-6, pp 605-608.

There are also numerous articles or patents describing the application of this technology especially for extracting squalene of vegetable origin (such as patent applications JP 2005/087998 from palm oil, or US 2004/0015033 from olive oil).

International patent application WO 94/026683 presents a method and a device for producing squalene from olive oil residues.

This method comprises the following four steps: saponification, cracking, esterification of the fatty acids and extraction with supercritical fluid.

However, for extraction with supercritical fluid, a product is used that has been esterified beforehand with metal catalysts, which is then sprayed into a high-pressure extraction tower provided with zones with variable temperatures.

These methods and devices make it possible to obtain marketable squalene with a purity of more than 90%, but are difficult to extrapolate to an industrial scale at attractive costs.

Very few documents describe the preferred methods for refining squalene produced by microalgae.

We may for example find the scientific article of LU et al., published in *Journal of Chromatography*, 2003, 994, 37-43, which extols the merits of high-speed countercurrent chromatography for the preparative separation and purification of squalene produced by *Thraustochytrium* ATCC 26185.

According to these authors, this technology has the merit of proposing a method that is far more efficient than the more conventional HPLC (high-performance liquid chromatography), as it proposes a single liquid/liquid chromatographic partition without solid support (and therefore without loss of material by irreversible adsorption on said solid support).

However, as is described in detail in this article, this method can only be envisaged at the scale of the laboratory, and moreover requires a preliminary step of extraction with methanol/chloroform.

In the state of the art, some preliminary work on extraction with supercritical fluid has been undertaken for *Botryococcus braunii*, *Scenedesmus obliquus* or *Torulaspora delbrueckii*.

However, the operating conditions recommended are also difficult to transfer to an industrial scale.

To the best knowledge of the applicant, no efficient method, suitable for industrial application, for refining squalene produced from microalgae, using technology of the supercritical fluid or molecular distillation type, is readily accessible to a person skilled in the art.

Anxious to develop an efficient method for refining squalene produced by microalgae, the applicant undertook its own research and succeeded in adapting the technologies for extraction with supercritical fluid and by molecular distillation so as to guarantee a squalene level above 95%, preferably above 97%, or even on the order of 100%.

This level of purity makes it possible to use the squalene thus obtained not only in the medical field, but also to envisage its easy hydrogenation to squalane for cosmetic applications.

The present invention therefore relates to a method for preparing a composition with high squalene content produced by fermentation of microorganisms, characterized in that it comprises a purification step selected from the group consisting of extraction with supercritical $CO_2$ in a multistage fractionating column operating in countercurrent with extract reflux, and so-called "short-path" molecular distillation.

The microorganisms are preferably microalgae belonging to the family Thraustochytriales sp., even more preferably microalgae belonging to the species *Schizochytrium* sp., *Aurantiochytrium* sp. and *Thraustochytrium* sp.

In the sense of the invention, "composition with high squalene content" means a composition having a squalene content above 95 wt %, preferably above 97 wt %, even more preferably on the order of 100 wt %.

Execution of Two Successive Steps of Extraction with Supercritical $CO_2$.

In this first preferred embodiment of the method according to the invention, a method is carried out, characterized in that it comprises the following steps:
1) preparing a biomass of microalgae belonging to the family Thraustochytriales,
2) treating the biomass so as to obtain a crude oil containing at least 10 wt % of squalene, preferably at least 15 wt % of squalene,
3) fractionating the crude oil thus obtained by contact with a fluid at supercritical pressure in a multistage fractionating column operating in countercurrent with extract reflux so as to produce an extract having a squalene content between 70 and 75% and a raffinate having less than 1.5% of squalene,
4) bringing the extract thus obtained into contact with a fluid at supercritical pressure in the same multistage fractionating column operating in countercurrent with extract reflux as that in step 3) so as to obtain a squalene content between 95 and 99 wt %, and
5) collecting the squalene composition thus obtained.

The first step of this first preferred embodiment consists of preparing a biomass of microalgae belonging to the family Thraustochytriales.

As microalgae belonging to the family Thraustochytriales, the following commercial strains are for example available:
*Schizochytrium* sp. referenced ATCC 20888, and
*Aurantiochytrium* sp. referenced ATCC PRA 276.

Moreover, the applicant also has its own production strain, a *Schizochytrium* sp. deposited on 14 Apr. 2011 in France at the Collection Nationale de Cultures de Microorganismes [National Collection of Cultures of Microorganisms] of the Institut Pasteur under No. CNCM I-4469 and also deposited in China at the CHINA CENTER FOR TYPE CULTURE COLLECTION of the University of Wuhan, Wuhan 430072, P.R. China under No. M 209118.

Culture is carried out in heterotrophic conditions. Generally, the culture step comprises a preculture step, for revivifying the strain, then a step of culture or of fermentation proper. This last-mentioned step corresponds to the step of production of the lipid compounds of interest.

The culture conditions of these microalgae are well known in the field.

For example, in the article of G. CHEN in *New Biotechnology*, 2010, 27-4, pp 382-389, a method is found comprising the following successive steps:
starting from the strain maintained on agar nutrient medium comprising glucose, monosodium glutamate, yeast extract and various trace elements,
carrying out a preculture in conical flasks on an orbital stirrer, at a pH of 6, at a temperature of 25° C. in order to obtain a revivified biomass, and
seeding another series of production conical flasks with the same culture medium as that used in preculture, with about 0.5% (v/v) of the biomass obtained in the preceding step, and maintaining the temperature at 25° C.

The second step of this first preferred embodiment consists of treating the biomass so as to obtain a crude oil containing at least 10 wt % of squalene, preferably at least 15 wt % of squalene.

Moreover, these treatments may be carried out by any method known by a person skilled in the art, and the squalene content of at least 10 wt % may be obtained from the strain CNCM I-4469 described above.

As will be described in the examples given below, the applicant recommends:
- adjusting the biomass to a dry matter content between 6 and 12%, preferably to a dry matter content between 10 and 12% with demineralized water,
- treating the biomass thus obtained using an enzyme of the Alcalase type so as to break the cell walls of said microalgae,
- adding ethanol at more than 5% (v/v), preferably about 10% (v/v) to the reaction mixture (in the form of oil-in-water emulsion),
- centrifuging the reaction mixture thus obtained in order to separate the oil from the aqueous phase, and
- recovering the oily upper phase enriched in squalene.

This enrichment is understood as a squalene content of at least 10 wt %, preferably of at least 15 wt %.

The third step of this first preferred embodiment consists of fractionating the crude oil thus obtained by contact with a fluid at supercritical pressure in a multistage fractionating column operating in countercurrent with extract reflux so as to produce an extract having a squalene content between 70 and 75% and a raffinate having less than 1.5% of squalene.

As far as the applicant knows, this particular form of extraction of squalene, using a multistage fractionating column operating in countercurrent with extract reflux, has never been exploited for squalene produced by fermentation of microorganisms in general, and for microorganisms of the type of microalgae belonging to the family Thraustochytriales in particular.

The applicant has thus taken advantage of the large difference in solubility between squalene (a nonpolar hydrocarbon) and the triglycerides constituting the lipids of the oil in carbon dioxide at supercritical pressure, squalene being much more soluble than the triglycerides.

For this purpose, the applicant found that the use of a multistage fractionating column operating in countercurrent with an extract reflux, the column being provided with structured packing, unexpectedly made it possible to achieve squalene of high purity with an excellent yield relative to the starting oil.

A person skilled in the art knows that extraction with a fluid at supercritical pressure leads to extracts of very high quality.

One of the main advantages of the methods employing fluids at supercritical pressure is the ease of performing separation between the solvent (the fluid) and the extracts and solutes, as has been described in numerous publications and, for certain important aspects of implementation, in French patent FR 2584618.

One of the other important advantages of supercritical fluids is their "adaptable" selectivity with respect to the components of a mixture.

This very high selectivity is linked to the particular properties of supercritical fluids, and particularly those of carbon dioxide at supercritical pressure: the solvent power may be finely controlled by varying the pressure and temperature of the fluid.

The applicant has verified that "mild" conditions are the most selective as the solvent becomes increasingly selective as its solvent power decreases.

Thus, the applicant recommends preferably using pure carbon dioxide, rather than added co-solvent, which would increase its solvent power.

Moreover, an operating pressure between 10 and 50 MPa is selected, preferably between 15 and 25 MPa, and a temperature between 40 and 80° C.

The fluid at supercritical pressure is pumped at high pressure by a pump and is raised to the desired temperature in a heat exchanger before being injected into the bottom of the column at a flow rate that is kept constant and is displayed on a mass flowmeter.

The feed is injected via a high-pressure pump in the middle of the column with structured packing, between sections 1 and 2, or 2 and 3, or 3 and 4, counting from the bottom of the column, at a flow rate that is kept constant and is displayed on a mass flowmeter.

The fluid laden with the extract leaves at the top of the column, after which it is partially decompressed to 6 MPa and sent to several separating stages, notably comprising cyclone separators mounted in series, the body of which is heated by circulation of water in a jacket.

The liquid extract is recovered at the bottom of these separators, whereas the fluid in the gaseous state is then recycled conventionally: condensation in a condenser cooled to 0 to 5° C., intermediate storage in a buffer flask whose liquid level is kept constant by feeding with fresh fluid from an external storage tank, pumping at high pressure and heating to the desired temperature.

The raffinate is withdrawn at the bottom of the column via an expansion valve controlled by a level sensor, thus keeping the oil-fluid interface in the lower part of the column; in order to avoid pressure jolts that are detrimental to fractionation in the column, this raffinate is collected in two settling tanks in series, the pressure in the first being maintained at a value less than about 1 to 4 MPa lower than the pressure prevailing in the column.

These tanks thus permit withdrawal of the raffinate without jolts with minimal losses of fluid dissolved in the raffinate.

As shown by the applicant, the use of multistage countercurrent contact between the separating fluid and the liquid feed allows the best utilization of this selectivity of the fluid used.

Moreover, extract reflux makes a notable contribution to the improvement in the overall selectivity of the fractionation operation.

Extract reflux is generated here and is carefully controlled by establishing a thermal gradient along the column when the diameter of the latter allows good heat transfer to the walls, between on the one hand the fluid in contact with the feed and on the other hand the hot water circulating in the jacket divided into several independent sections to allow this gradient to be applied.

In fact, the solubility of most organic compounds in carbon dioxide at supercritical pressure, fixed in a zone ranging from the critical pressure (i.e. 7.4 MPa) to 30 MPa, decreases when the temperature increases; thus, when the fluid rises in the column in countercurrent with the oil, it can be heated, thus causing demixing of a portion of the extract and its reflux mixed with the oil.

If columns with a diameter larger than 200 mm are used, heat transfer to the walls becomes insufficient and it is preferable to employ an external extract reflux, a portion of the extract being separated at the top of the column by partial decompression of the fluid leaving the column, this fraction of liquid extract then being recompressed by a pump and injected at the top of the column.

Moreover, fluids at supercritical pressure have excellent properties of heat and mass transfer, far better than those of liquids, contributing to the excellent selectivity observed.

The fourth step of this first preferred embodiment consists of bringing the extract thus obtained into contact with a fluid at supercritical pressure in the same multistage fractionating column operating in countercurrent with extract reflux as that in step 3) so as to obtain a squalene content between 95 and 99 wt %.

This step of squalene enrichment is carried out in conditions similar to those of the preceding step, but in slightly different conditions of pressure and temperature.

Thus, an operating pressure is selected between 10 and 30 MPa, preferably between 10 and 20 MPa, and a temperature between 40 and 80° C.

The fifth step of this first preferred embodiment finally consists of collecting the squalene composition thus obtained.

As will be explained in the examples given below, the composition thus purified may have a squalene content greater than or equal to 97%.

Application of Molecular Distillation

In a second preferred embodiment of the method according to the invention, a method is carried out, characterized in that it comprises the following steps:
1) preparing a biomass of microalgae belonging to the family Thraustochytriales,
2) treating the biomass so as to obtain a crude oil containing at least 10 wt % of squalene, preferably at least 15 wt % of squalene,
3) optionally refining the crude oil thus obtained by a sequence of steps of degumming, deacidification, bleaching and deodorizing,
4) extracting the squalene by so-called "short-path" molecular distillation so as to obtain a light fraction having a squalene content above 60 wt %, preferably above 80 wt %,
5) refining this light fraction by a sequence of steps of saponification, two-phase separation, washing, bleaching and deodorizing, so as to obtain a raffinate having a squalene content between 95 and 100%, and
6) collecting the squalene composition thus obtained.

The first and second step of this second preferred embodiment of the method according to the invention are identical to the first and the second step of the first preferred embodiment presented above.

The crude oil thus obtained consists of glycerides (predominantly triglycerides), unsaponifiable substances (predominantly squalene) and optionally minor proportions of free fatty acids and phospholipids.

This crude oil may undergo coarse refining prior to extraction of the squalene by molecular distillation.

One or more of the following steps may be envisaged:
degumming: which allows removal of the pholipids by precipitation in an acid medium;
deacidification: which provides neutralization of the free fatty acids by the use of a base;
bleaching: conventionally performed with activated charcoal; or
deodorizing: by vacuum distillation, so-called steam "stripping".

These refining steps are the steps commonly used in the refining of vegetable oil.

The fourth step of this second preferred embodiment of the method according to the invention consists of extracting the squalene by so-called "short-path" molecular distillation so as to obtain a light fraction having a squalene content above 60 wt %, preferably above 80 wt %.

The squalene of the crude oil, optionally refined, is extracted by molecular distillation.

For a high vacuum, below 0.1 mbar, the boiling point of squalene is on the order of 200° C.

This high vacuum makes it possible to limit the temperature and thus limit the risks of degradation/polymerization of the squalene.

Moreover, the residence time is kept very short, less than one minute.

In this pressure-temperature-contact time regimen, the triglyceride fraction (high molecular weight) is not volatile.

Thus, the applicant found that, in these conditions, so-called "short-path" molecular distillation is a particularly suitable technology for separating these two fractions that are predominantly triglycerides and squalene.

The operating conditions recommended by the applicant are as follows.

From the nitrogen-inerted feed tank, the oil is pumped through a first circuit with thermostatic control in a range from 25 to 100° C. to the degasser (removal of traces of water and solvent).

At the degasser outlet, the oil is pumped into the "short-path" evaporation chamber through a circuit with thermostatic control in a temperature range from 50 to 150° C.

The temperature of the evaporator is adjusted in a range from 150 to 250° C.

The condenser is controlled in a temperature range from 0 to 50° C.

The pressure in the evaporation chamber is adjusted in a range from $10^{-2}$ to $10^{-4}$ mbar.

The distillate containing predominantly squalene and the residue containing predominantly the triglycerides are conveyed via the collecting circuits to the inerted storage tanks.

The squalene content in the light fraction of the distillate is above 60 wt %, preferably above 80 wt %.

The fifth step of this second preferred embodiment of the method according to the invention consists of refining this light fraction by a sequence of steps of saponification, two-phase separation, washing, bleaching and deodorizing, so as to obtain a raffinate having a squalene content between 95 and 100%.

Saponification is carried out beforehand in order to hydrolyze the residual glycerides possibly entrained during distillation but also to hydrolyze the esterified sterols.

The latter, then in free form (more polar), will be more easily removed during the next steps.

Saponification is carried out with ethanolic potash at a temperature of about 80° C. for a time from 0.5 to 2 h.

After cooling, the two phases of the mixture resulting from saponification may then be separated by decanting or centrifugation.

Emulsification is likely to make separation more complex; adding water may then facilitate separation.

The ethanolic phase concentrates the free fatty acids but also a proportion of the polar impurities generated. The oily phase concentrates the squalene.

The squalene phase separated after saponification is washed with water.

Several successive washings may be carried out.

Basic water (treated with potash or soda) may be used to entrain the residual saponification impurities during the first washing cycle(s).

Washing is completed when the supernatant from washing with water is at neutral pH.

Between each cycle, the phases (wash water and squalene) are separated by decanting or centrifugation.

At this stage, the squalene fraction is purified from a proportion of the sterols as well as the residual glycerides (mono-, di-, triglycerides).

An additional bleaching step may be carried out at this stage in order to reduce the yellowish coloration.

This bleaching step is carried out on activated charcoal similarly to the bleaching used conventionally in vegetable oil refining.

Refining of the squalene fraction ends with a deodorizing step.

Deodorizing is carried out by hot (150-200° C.) steam "stripping" under vacuum for a time from 0.5 to 1 h.

The squalene thus purified is stored under controlled atmosphere (ideally inerted with nitrogen).

Addition of antioxidants may be favorable for stabilization of this fraction.

The invention also relates to the use of a squalene composition obtained by carrying out a method according to the invention in the cosmetics, pharmaceutical and medical fields.

The invention further relates to a method for preparing a squalane-enriched composition by hydrogenation of the high-purity squalene composition obtained by carrying out a method according to the invention, as well as the use of this squalane composition in the cosmetics field.

The invention will be better understood from the examples given below, which are supplied for purposes of illustration and are nonlimiting.

EXAMPLE 1

Preparation of an Oil Containing at Least 10 Wt % of Squalene by Fermentation of a Microalga Belonging to the Family Thraustochytriales, in a 20-Liter Fermenter This example illustrates the method for extracting a squalene-enriched oil produced by fermentation of the microalga *Schizochytrium* sp. belonging to the applicant (deposited on 14 Apr. 2011 in France at the Collection Nationale de Cultures de Microorganismes [National Collection of Cultures of Microorganisms] of the Institut Pasteur under No. CNCM I-4469).

Fermentation was carried out here in two successive preliminary preculture phases before the culture/production phase proper in a 20-liter reactor.

For these experiments, addition of vitamins was provided in the first preculture medium, but was optional in the second preculture medium and in production.

The preculture media then had the composition presented in the following Tables I and II:

TABLE I

| First preculture medium | % |
|---|---|
| Glucose | 3 |
| Yeast extracts | 0.4 |
| Sodium glutamate | 6.42 |
| NaCl | 1.25 |
| $MgSO_4$ | 0.4 |
| KCl | 0.05 |
| $CaCl_2$ | 0.01 |
| $NaHCO_3$ | 0.05 |
| $KH_2PO_4$ | 0.4 |
| Mixture of vitamins | 0.14 |
| Trace elements | 0.8 |

TABLE II

| Second preculture medium | % |
|---|---|
| Glucose | 8.57 |
| Sodium glutamate | 6.42 |
| Yeast extracts | 0.64 |
| NaCl | 2 |
| $KH_2PO_4$ | 0.64 |
| $MgSO_4$ | 2.29 |
| $CaCl_2$ | 0.03 |

TABLE II-continued

| Second preculture medium | % |
|---|---|
| $NaHCO_3$ | 0.03 |
| $Na_2SO_4$ | 0.03 |
| Mixture of vitamins | 0.14 |
| Trace elements | 0.2 |

Generally, Clerol FBA 3107 antifoaming agent was used at 1 ml/l. Optionally, 50 mg/l of penicillin G sodium salt was used in order to prevent growth of contaminating bacteria.

The glucose was sterilized with $KH_2PO_4$, separately from the rest of the medium, thus avoiding formation of a precipitate (Ammonium-Phosphate-Magnesium). The mixture of vitamins and the trace elements were added after sterilizing filtration. The composition of the culture/production medium is given in Table III below.

TABLE III

| | % |
|---|---|
| Glucose, addition at T0 | 7.5 |
| Urea | 1 |
| Yeast extracts | 1.2 |
| NaCl | 0.25 |
| $KH_2PO_4$ | 0.96 |
| $MgSO_4$ | 1.2 |
| $CaCl_2$ | 0.12 |
| $NaHCO_3$ | 0.12 |
| KCl | 0.08 |
| Addition of the mixture of vitamins | 0.4 |
| Trace elements | 0.56 |

The composition of the mixtures of vitamins and of the trace elements is given in the following Tables IV and V:

TABLE IV

| Mixture of vitamins | g/L |
|---|---|
| B1 | 45 |
| B6 | 45 |
| B12 | 0.25 |

TABLE V

| Trace elements | g/L |
|---|---|
| $MnCl_2 \cdot 2H_2O$ | 8.60 |
| $CoCl_2 \cdot 6H_2O$ | 0.2 |
| $NiSO_4 \cdot 6H_2O$ | 7.50 |
| $Na_2MoO_4 \cdot 2H_2O$ | 0.15 |
| $ZnSO_4 \cdot 7H_2O$ | 5.70 |
| $CuSO_4 \cdot 5H_2O$ | 6.50 |
| $FeSO_4 \cdot 7H_2O$ | 32.00 |
| $ZnCl_2$ | 1.50 |

Preculture Conditions

The first preculture was carried out in 500-ml conical flasks equipped with baffles, to which a drop of CLEROL FBA 3107 antifoaming agent marketed by the company COGNIS GmbH Düsseldorf was added.

The culture medium was filtered after complete dissolution of its constituents, optionally supplemented with penicillin G sodium salt at a rate of 0.25 mg/l.

Inoculation was carried out by taking colonies of microalgae cultured in a Petri dish (at a rate of one 10-μl loop).

Incubation took 24 to 36 hours, at a temperature of 28° C., with stirring at 100 rpm (on an orbital stirrer).

As the biomass decants (or adheres to the wall), we were careful to take 3 to 5 ml after stirring the conical flask well.

For the second preculture, 2-liter conical flasks were used, equipped with baffles and pipework.

One drop of antifoaming agent and the yeast extract were added to 100 ml of water.

All the constituents of the medium were filtered after dissolution in 300 ml of demineralized water. Penicillin G sodium salt could optionally be added, and in the conical flask a drop of antifoaming agent was added prior to its sterilization.

Seeding was then carried out with 3 to 5 ml of the first preculture.

Incubation was carried out at 28° C. for a further 24 to 36 hours, with stirring at 100 rpm.

Production in a 20-Liter Reactor

Culture proper was carried out as follows in a 20-liter reactor:
- sterilization of the medium for one part in the reactor, and separately for the other part so as to avoid formation of a precipitate,
- seeding carried out with the biomass produced at the end of the second preculture at a rate of 0.5% v/v of the culture medium,
- culture maintained at 30° C.,
- rate of transfer of oxygen fixed at 35-40 mmol/l/h,
- aeration at 0.2 to 0.3 VVM,
- initial pH >5.5, and
- feed of glucose once the concentration is >20%, so as to maintain a glucose concentration between 15 and 70 g/l.

The following Table VI shows the results obtained with the applicant's *Schizochytrium* sp.

TABLE VI

| Tests | E |
|---|---|
| Temperature of the precultures (° C.) | 28 |
| Culture temperature (° C.) | 30 |
| Squalene titer at the end of culture (g/l) | 4.4 |
| Biomass (g/l) | 54 |
| g/100 g of squalene to dry biomass | 8.2 |

Biomass Recovery

The biomass is removed from the fermenter and washed from interstitial soluble matter by a succession of two concentration series by centrifugation (5 minutes at 5000 g) and dilution of the biomass (at a rate of ⅓ Vpellet/Vwater).

The dry cell concentration to total crude dry matter is 95%.

The dry matter is then adjusted to 12% with distilled water.

Obtaining Squalene-Enriched Crude Oil

The washed biomass is stirred in a laboratory reactor of the 2-liter fermenter type (such as those marketed by the company Interscience) equipped with a marine propeller and baffles.

This system makes it possible to limit emulsification of the cellular lysate generated while permitting good mixing, which is indispensable for the action of the lytic enzyme.

The temperature is adjusted to 60° C. and the pH is controlled to about 8 with soda.

These conditions are optimal for the activity of the Alcalase enzyme (Novozymes) added at a level of 1%/s.

The lysis time is fixed at 4 h.

At the end of lysis, 10% of ethanol ($V_{ethanol}/V_{lysate}$) is added to the reaction mixture (oil-in-water emulsion), which is stirred for an additional 15 min.

The lysate is centrifuged for 5 minutes at 12000 g. The oil containing the squalene, which has dephased at the surface, is thus extracted.

EXAMPLE 2

Preparation of an Oil Containing at Least 10 Wt % of Squalene by Fermentation of a Microalga Belonging to the Family Thraustochytriales, in a 1-m³ Fermenter Starting from production carried out in a 1-m³ fermenter (fermentation conditions similar to those in example 1), the biomass is extracted from the fermenter by a SEEPEX positive-displacement pump feeding a Flottweg S3E Sédicanteur (clarifier).

In this way the biomass is concentrated to 200 g/l.

The concentrate is diluted in a 1-m³ tank with decarbonated water (1 volume of water/volume of concentrate) and then concentrated again by the same operation as described previously to obtain 620 kg of biomass washed and concentrated to 110 g/l.

The biomass is stirred at 150 rpm in a 1-m³ tank, and is heated to 60° C.

The pH is then adjusted to 8 with 45% potash.

The enzyme Alcalase 2.4 L FG from NOVO is added at a level of 1% (/dry biomass). The lysis parameters are maintained for 6 h.

The quality of lysis is monitored with a light microscope and by centrifugation of samples (2 min, 10000 g).

At the end of lysis, 60 l of ethanol (~10% vol/vol) are added to the tank maintained at 60° C. with stirring.

In the same way as in example 1, the temperature is then raised to 80° C. again and centrifugation is then carried out on the ALPHA LAVAL CLARA 20 centrifugation unit, configured in concentrator mode with 3 outlets.

This configuration is particularly suitable for separation of a three-phase mixture of the solid/liquid/liquid type.

Rotating at 9600 rev/min makes it possible to reach about 10,000 g.

Feed of cellular lysate is provided using a positive-displacement pump at a flow rate of 100 to 400 l/h.

The interface between the heavy phase and the light phase is displaced by controlling the counterpressure at the heavy phase outlet.

The frequency of auto-desliming is adjusted to a frequency of 2 to 15 min.

13 kg of squalene-rich crude oil is thus recovered at a yield of more than 50%.

EXAMPLE 3

Extraction of Squalene by Molecular Distillation

A crude oil containing 21.8% of squalene is obtained by extraction from a biomass of microalgae prepared according to example 2.

From the nitrogen-inerted feed tank, 8 kg of oil is pumped at 3.5 kg/h to the degasser at a temperature of 120° C.

At the degasser outlet, the oil goes through the "short-path" evaporation chamber via a circuit maintained at 85° C. The temperature of the evaporator is adjusted to 220° C.

The condenser is adjusted to a temperature of 20° C. The maximum vacuum is produced in the evaporation chamber ($<10^{-3}$ mbar).

The distillate containing squalene and the residue containing the triglycerides are conveyed via the collecting circuits to the inerted storage tanks. At this stage, about 1.5 kg of distillate and 6 kg of residue are recovered.

The squalene content (percentage by weight based on NMR analysis) in the distillate is equal to 94%.

The squalene content of the residue is below 2%.

The sequence of refining operations is carried out here starting from a sample of 10 g of squalene extracted by molecular distillation as described above.

The saponification operation is carried out in a medium containing potash (2N) maintaining the ratio ½ ($m_{oil}/m_{ethanolic\ potash}$) with ethanolic solvent (ratio 9/1 ($m_{ethanol}/m_{water}$)).

The saponification medium is maintained at 80° C. under reflux for 45 min.

The content of free fatty acid thus increases from 0.29 to 3.1 $g_{oleic\ acid\ eq.}/\% g_{oil}$).

These free fatty acids are derived partly from hydrolysis of the esterified sterols.

The two phases of the partially emulsified saponification mixture are separated by centrifugation (10 min at 25 000 g).

The extracted oily phase (squalene) is washed with water with a small addition of potash (ratio 3/1 ($m_{water}/m_{oil}$)).

Washing is repeated with clean water until a supernatant at neutral pH is obtained.

Separation between each washing step is carried out by centrifugation for 10 min at 25,000 g.

7 g of squalene is obtained at this stage with a yield of 70%.

The fraction purified by saponification is bleached with activated charcoal (5%/oil) with stirring, and then the activated charcoal is separated by filtration at 0.2 μm.

The final step of deodorizing is carried out by steam stripping at 180° C. under vacuum for 30 min.

The purified squalene thus obtained has a purity close to 98%.

The resolution of the NMR analysis does not allow a precise value of purity to be obtained but allows the rate of removal of impurities to be evaluated at around 75%.

EXAMPLE 4

Refining of Squalene by Carrying Out Two Successive Steps of Extraction with Supercritical $CO_2$ This used 200 liters of oil containing more than 15% of squalene produced from *Schizochytrium* algae cultured in a 10-m³ fermenter in operating conditions close to examples 1 and 2.

This oil contains more particularly triglycerides mainly with fatty acids:

C14, C16 short-chain to 27%,
C20 and especially C22 long-chain to 43% and
a large amount of unsaponifiable substances essentially consisting of squalene (~15.5%).

The aim is to obtain on the one hand squalene purified to more than 95% and on the other hand an oil from which squalene has been removed.

The method of fractionation employed according to the invention therefore comprises two steps that may be summarized thus:

Step 1: Fractionation of the crude oil by contact with a fluid at supercritical pressure yielding a squalene-rich extract and a squalene-free raffinate; and Step 2: Purification of the squalene by fractionation of the extract obtained in step 1 by contact with a fluid at supercritical pressure.

This fractionation is based on the large difference in solubility between squalene (a nonpolar hydrocarbon) and the triglycerides constituting the lipids of the oil, squalene being far more soluble than the triglycerides.

The two fractionation steps are performed in a packed fractionating column operating in countercurrent with internal extract reflux.

The fractionating unit employed is equipped with a countercurrent fractionating column with an inside diameter of 125 mm and a height of 8 m allowing establishment of a temperature gradient in 4 sections of 2 m.

This column is filled with high-performance packing (Sulzer BX type). This unit is fully automated and offers continuous operation.

Step 1: Treatment of the Crude Oil in Order to Extract the Squalene

The oil is fed into the column between sections 3 and 4, counting from the bottom of the column The process parameters are presented in the following Table VII.

TABLE VII

| Purification of SQUALENE | Step 1 |
| --- | --- |
| Pressure (bar) | 200 |
| Temperature (° C.) of the 4 sections | 40/50/50/72 |
| $CO_2$ flow rate (kg/h) | 185 |
| Flow rate of the feed (kg/h) | 5 |
| Level of solvent (kg$CO_2$/kg oil) | 37 |
| Fraction collected | Extract Raffinate |
| Fraction/Feed | 20% (Extract) 80% (Raffinate) |
| Squalene content | 72% (Extract) |

The squalene is thus recovered in the extract at a relatively high concentration.

Treatment of the crude oil makes it possible to extract most of the squalene.

Step 2: Purification of Squalene

Supercritical fractionation of squalene is carried out once again in conditions similar to those used for the crude oil, but with slightly different conditions of pressure and temperature as indicated in the following Table VIII.

TABLE VIII

| Purification of SQUALENE | Step 2 |
| --- | --- |
| Pressure (bar) | 175 |
| Temperature (° C.) of the 4 sections | 40/50/50/72 |
| $CO_2$ flow rate (kg/h) | 200 |
| Flow rate of the feed (kg/h) | 5 |
| Level of solvent (kg$CO_2$/kg oil) | 40 |
| Fraction collected | Extract |
| Fraction/Feed | 58% |
| Squalene content | 97% |

This method employing two successive steps of extraction with supercritical $CO_2$ makes it possible to guarantee obtaining a composition with a squalene content of 97%.

The invention claimed is:

1. A method for preparing a composition with a squalene content above 95 wt % produced by fermentation of a microalgae belonging to the family Thraustochytriales, wherein said method comprises the following steps:

a) preparing a biomass of said microalgae,
b) treating the biomass so as to obtain a crude oil containing at least 10 wt % of squalene,
c) optionally refining the crude oil thus obtained by a sequence of steps of degumming, deacidification, bleaching and deodorizing,
d) extracting the squalene by "short-path" molecular distillation so as to obtain a light fraction having a squalene content above 60 wt %,
e) refining this light fraction by a sequence of steps of saponification, two-phase separation, washing, bleaching and deodorizing, so as to obtain a raffinate having a squalene content between 95 and 100%, and
f) collecting the squalene composition thus obtained.

2. The method of claim 1, wherein the microalgae belonging to the family Thraustochytriales is a *Schizochytrium* sp., *Aurantiochytrium* sp. or *Thraustochytrium* sp.

3. A method for preparing a composition with a squalene content above 95 wt %, said method comprising the following steps:
1) preparing a biomass of microalgae belonging to the family Thraustochytriales,
2) treating the biomass so as to obtain a crude oil containing at least 10 wt % of squalene,
3) fractionating the crude oil thus obtained by contact with a fluid at supercritical pressure in a multistage fractionating column operating in countercurrent with extract reflux so as to produce an extract having a squalene content between 70 and 75% and a raffinate having less than 1.5% of squalene,
4) bringing the extract thus obtained into contact with a fluid at supercritical pressure in the same multistage fractionating column operating in countercurrent with extract reflux as that in step 3) so as to obtain a squalene content between 95 and 99 wt %, and
5) collecting the squalene composition thus obtained.

4. The method of claim 3, characterized in that the multistage fractionating column operating in countercurrent is a column with structured packing.

5. The method of claim 3, characterized in that the fluid at supercritical pressure employed in step 3) is raised to a pressure between 10 and 50 MPa and to a temperature between 40 and 80° C.

6. The method of claim 3, characterized in that the fluid at supercritical pressure employed in step 4) is raised to a pressure between 10 and 30 MPa and to a temperature between 40 and 80° C.

7. The method of claim 3, characterized in that the fluid at supercritical pressure is pure carbon dioxide.

8. The method of claim 1, wherein step 4) of molecular distillation is carried out under high vacuum, at a value below 0.1 mbar.

9. The method of claim 1, wherein "short-path" means contacting for a time of less than 1 minute.

10. A method for preparing a cosmetic or pharmaceutical composition comprising adding a squalene composition obtained by carrying out a method according to claim 1 to a cosmetic or pharmaceutical composition.

11. A method for preparing a squalane-enriched composition by hydrogenation of the high-purity squalene composition obtained by carrying out a method according to claim 1.

12. A method for preparing a cosmetic composition comprising adding a squalane composition obtained by carrying out a method of claim 11.

13. The method of claim 3, wherein the microalgae belonging to the family Thraustochytriales is a *Schizochytrium* sp., *Aurantiochytrium* sp. or *Thraustochytrium* sp.

* * * * *